USOO5099026A

United States Patent [19]

Crater et al.

[11] Patent Number: 5,099,026
[45] Date of Patent: Mar. 24, 1992

[54] FLUOROCHEMICAL OXAZOLIDINONES

[76] Inventors: Davis H. Crater; Richard D. Howells; Richard M. Stern; John A. Temperante, all of P.O. Box 33427, St. Paul, Minn. 55133-3427

[21] Appl. No.: 652,461

[22] Filed: Feb. 7, 1991

Related U.S. Application Data

[63] Continuation of Ser. No. 481,670, Feb. 14, 1990, abandoned, which is a continuation of Ser. No. 235,757, Aug. 18, 1988, abandoned, which is a continuation of Ser. No. 906,817, Sep. 12, 1986, abandoned.

[51] Int. Cl.$^5$ .................................. C07D 263/04
[52] U.S. Cl. .................................. 548/229
[58] Field of Search .................................. 548/229

[56]  References Cited

U.S. PATENT DOCUMENTS

| Re. 30,721 | 8/1981 | Heiss | 524/95 |
|---|---|---|---|
| 3,190,885 | 6/1965 | Hickner | 524/95 |
| 3,450,674 | 6/1969 | Walles | 260/77.5 |
| 3,458,527 | 7/1969 | Schramm | 524/95 |
| 3,461,129 | 8/1969 | Middleton | 548/225 |
| 3,899,563 | 8/1975 | Oxenrider et al. | 264/211 |
| 4,128,654 | 12/1978 | Fugitt et al. | 424/727 |
| 4,215,205 | 7/1980 | Landucci | 525/331 |
| 4,426,466 | 1/1984 | Schwartz | 523/455 |
| 4,468,527 | 8/1984 | Patel | 564/96 |
| 4,540,497 | 9/1985 | Chang et al. | 252/8.8 |
| 4,566,981 | 1/1986 | Howells | 252/8.8 |
| 4,588,694 | 5/1986 | Hamaguchi | 435/280 |
| 5,025,052 | 6/1991 | Crater et al. | 524/104 |

FOREIGN PATENT DOCUMENTS

| 518917 | 11/1955 | Canada | 524/95 |
|---|---|---|---|
| 0127902 | 12/1984 | European Pat. Off. | |
| 46-21948 | 6/1971 | Japan | 524/95 |

OTHER PUBLICATIONS

CAS 103:37470z.
CAS 100:190343t.
Grant, "Hackh's Chemical Dictionary", 4th ed., pp. 312, 481, McGraw-Hill, NY, 1972.
Banks, Ed., Organofluorine Chemicals and Their Industrial Applications, Ellis Horwood Ltd., Chichester, England, 1979, pp. 226-234.
Mares, F., et al., Modification of Fiber Surfaces by Monomeric Additives, Part I: Extrusion Techniques, Textile Research Journal, vol. 47, No. 8, pp. 551-561.
Mares, F., et al., Modification of Fiber Surfaces by Monomeric Additives, Part II: Absorption of Fluorocarbon Additives by Polyethylene Terephthalate, Textile Research Journal, vol. 48, No. 4, pp. 218-229.
Knunyants, I. L., et al., 3-Fluoroalkyl-2-Oxazolidinones, Zh. Vses. Khim. O-va, 24(6), 1979, p. 662.
Iwakura, Y., et al., Polyoxazolidones, Journal of Polymer Science; part A-1; vol. 5, 1967, pp. 1865-1880.
Iwakura, Y., et al., Glycidyl Ether Reactions with Urethanes and Ureas. A New Synthetic Method for 2-oxazolidones, Journal of Organic Chemistry, vol. 29, 1964, pp. 379-382.
Kordomenos, P. I., et al., Oxazolidone Coatings, Part I: Synthesis and Structure, Journal of Coatings Technology, vol. 55, No. 700, 1983, pp. 49-57.
Kordomenas, P. I., et al., Oxazolidone Coatings, Part II: Structure-Properties Relationships and Thermal Stability, Journal of Coatings Technology, vol. 55, No. 700, 1983, pp. 59-61.
Wente, Van A., Superfine Thermoplastic Fibers, Ind. & Eng. Chem., vol. 48, No. 8, 1956, pp. 1342-1346.
Naval Res. Lab. Report 111437, 4/15/54.

Primary Examiner—Paul R. Michl
Assistant Examiner—Yong S. Lee
Attorney, Agent, or Firm—Gary L. Griswold; Walter N. Kirn; Carole Truesdale

[57]  ABSTRACT

Fluorochemical oxazolidinone compositions are provided. They are normally solid, water-insoluble, fluoroaliphatic radical-containing 2-oxazolidinone compounds which have one or more 2-oxazolidinone moieties, at least one of which has a monovalent fluoroaliphatic radical bonded to the 5-position carbon atom thereof by an organic linking group.

7 Claims, No Drawings

FLUOROCHEMICAL OXAZOLIDINONES

This is a continuation of application Ser. No. 07/481,670 filed Feb. 14, 1990 now abandoned, which is a continuation of application Ser. No. 07/235,757 filed Aug. 18, 1988 now abandoned, which is a continuation of application Ser. No. 906,817 filed Sept. 12, 1986 now abandoned.

This invention relates to fluorochemical compositions, the process for preparing the fluorochemical compositions, fibrous substrates treated with the fluorochemical compositions to provide oil and water repellency, and to melt extrusion of fibers and films containing the fluorochemical compositions.

The use of various fluorochemical compositions on fibers and fibrous substrates, such as textiles, paper, and leather, to impart oil and water repellency is known. See, for example, Banks, Ed., *Organofluorine Chemicals and Their Industrial Applications*, Ellis Horwood Ltd., Chichester, England, 1979, pp. 226-234. Such fluorochemical compositions include, for example, fluorochemical guanidines (U.S. Pat. No. 4,540,497, Chang et al.), compositions of cationic and non-cationic fluorochemicals (U.S. Pat. No. 4,566,981, Howells), compositions containing fluorochemical carboxylic acid and epoxidic cationic resin (U.S. Pat. No. 4,426,466, Schwartz), fluoroaliphatic carbodiimides (U.S. Pat. No. 4,215,205, Landucci), and fluoroaliphatic alcohols (U.S. Pat. No. 4,468,527, Patel).

Fluorochemical compositions can be applied to various fibrous substrates by methods which include, for example, spraying, padding, and finish bath immersion. Textile fibers and yarns can also be treated by incorporation of the fluorochemical in fiber spin finishes and by melt extrusion of a blend of a synthetic organic fiber-forming polymer and a fluorochemical composition. Such melt extrusion is described, for example, by Mares, F., et al., "Modification of Fiber Surfaces by Monomeric Additives, Part I : Extrusion Techniques," *Textile Research Journal*, Vol. 47, No. 8, pp. 551-561 and Mares, F., et al., "Modification of Fiber Surfaces by Monomeric Additives, Part II : Absorption of Fluorocarbon Additives by Polyethylene Terephthalate", *Textile Research Journal*, Vol. 48, No. 4, pp. 218-229, and in U.S. Pat. No. 3,899,563 (Oxenrider et al.)

Oxazolidinone compounds, sometimes referred to as oxazolidones, and processes for preparing oxazolidinone compounds have been described, for example, in Knunyants, I.L., et al., "3-Fluoroalkyl-2-Oxazolidinones", *Zh. Vses. Khim. O-va.*, 24(6), 1979, p. 662 [CA92:110905f]; Iwakura, Y., et al., "Polyoxazolidones", *Journal of Polymer Science;* Part A-1; Vol. 5, 1967, pp. 1865-1880; Iwakura, Y., et al., "Glycidyl Ether Reactions with Urethanes and Ureas. A New Synthetic Method for 2-Oxazolidones", *Journal of Organic Chemistry*, Vol. 29, 1964, pp. 379-382; Kordomenos, P.I., et al., "Oxazolidone Coatings. Part I : Synthesis and Structure", *Journal of Coatings Technology*, Vol. 55, No. 700, 1983, pp. 49-57; Kordomenas, P.I., et al., "Oxazolidone Coatings, part II : Structure-Properties Relationships and Thermal Stability," *Journal of Coatings Technology*, Vol. 55, No. 700, 1983, pp. 59-61.

This invention provides fluorochemical oxazolidinone compositions or fluorochemical oxazolidinones comprising normally solid, water-insoluble, fluoroaliphatic radical-containing 2-oxazolidinone compounds, said compounds comprising one or more 2-oxazolidinone moieties,

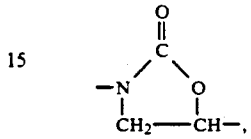

at least one of which has a monovalent fluoroaliphatic radical, $R_f$, bonded to the 5-position carbon atom thereof by an organic linking group. This invention also provides a process for preparing the fluorochemical oxazolidinone compositions.

This invention further provides compositions comprising aqueous suspensions or emulsions, or organic solvent solutions, of the fluorochemical oxazolidinone compositions, which compositions are useful in the surface treatment of fibrous substrates, such as textile fibers (or filaments) during their manufacture, and useful also in the surface treatment of finished or fabricated fibrous substrates such as textiles, carpets, paper and leather, to impart oil and water repellency and anti-soiling properties thereto.

This invention also provides fibers, films, and molded articles prepared by melt extrusion and molded articles prepared by, e.g., injection molding of a blend or mixture of (a) fiber- or film-forming synthetic organic polymers and (b) fluorochemical oxazolidinones which fibers, films, and molded articles have low surface energy, oil and water repellency, and anti-soiling properties.

A class of fluoroaliphatic radical-containing oxazolidinone compounds of this invention can be represented by the Formula I.

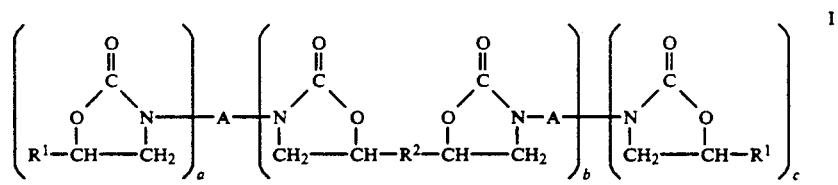

where each $R^1$ is independently hydrogen or an organic radical, which organic radical can contain -Q-$R_f$ where Q is a linking group and $R_f$ is a fluoroaliphatic radical, each $R^2$ is independently an organic radical, which organic radicals can contain -Q-$R_f$ where Q and $R_f$ are as defined above, with the proviso that there is at least one $R_f$ radical in one of $R^1$ and $R^2$, each A is independently an organic radical, a is zero or 1, b is a number from 0 to about 6, c is 0, 1 or 2, and the sum of a+b+c is at least 1.

In Formula I, each $R^1$ is independently H or an organic radical and can be selected from alkyl, cycloalkyl, aryl and combinations thereof, e.g., aralkyl, and can contain halogen atoms, fluoroaliphatic radicals, $R_f$, and one or more hetero atoms or hetero atom-containing moieties, e.g. —O—, —S—, —SO—, —SO$_2$.

and —CO—, and is preferably free from active hydrogen atoms (i.e., hydrogen atoms of groups such as hydroxyl, amino, mercapto and carboxyl that can readily react with isocyanate under urethane bond-forming conditions, e.g. 20°-100° C.). Suitable $R^1$ groups have up to 20 carbon atoms and include, for example, H—, ClCH$_2$—, C$_6$H$_5$—, C$_6$H$_5$OCH$_2$—, C$_8$F$_{17}$SO$_2$N(CH$_3$)CH$_2$—, C$_6$F$_{13}$CH$_2$CH$_2$OCH$_2$—, and C$_{10}$F$_{21}$CH$_2$CH$_2$SCH$_2$CH$_2$OCH$_2$—.

In Formula I, $R^2$ is a divalent organic linking group which can be selected from alkylene groups such as ethylene, propylene, hexylene, and methylene dicyclohexylene, having 2 to about 20 carbon atoms, aralkylene groups, such as —CH$_2$C$_6$H$_4$CH$_2$— and —C$_6$H$_4$CH$_2$C$_6$H$_4$—, having up to 20 carbon atoms, arylene groups, such as tolylene and various combinations of these groups. The $R^2$ groups can also contain $R_f$ radicals and one or more hetero atoms or hetero atom-containing moieties, e.g., —O—, —S—, —SO—, —SO$_2$—,

and —CO—, and are preferably free of active hydrogen atoms. Suitable $R^2$ groups include, for example, —CH$_2$O(CH$_2$)$_4$OCH$_2$—, —CH$_2$OCOC$_6$H$_4$COOCH$_2$—, —CH$_2$OC$_6$H$_4$(CH$_3$)$_2$C$_6$H$_4$OCH$_2$—, C$_8$F$_{17}$SO$_2$N(CH$_2$—)$_2$, C$_6$F$_{13}$CON(CH$_2$—)$_2$.

The organic linking group A in Formula I is a mono-, di- or polyvalent organic radical, such as alkyl (e.g. butyl, hexyl), aryl (e.g. phenyl), aralkyl (e.g. tolyl); alkylene (e.g. ethylene, hexamethylene), arylene (e.g. tolylene) or aralkylene (e.g., —CH$_2$C$_6$H$_4$CH$_2$— and —C$_6$H$_4$CH$_2$C$_6$H$_4$—). The organic linking groups can have up to 20 carbon atoms and can contain one or more of the hetero atoms or hetero atom-containing moieties, e.g., —O—, —S—, —SO—, —SO$_2$—,

and —CO—, and are preferably free of said active hydrogen atoms.

The A group can be the residue of an organic isocyanate from which the oxazolidinone moieties are formed. That is, A is the residue of an organic isocyanate exclusive of the isocyanate functional group. Isocyanates useful in preparing the oxazolidinones of this invention include, for example, monoisocyanates such as phenyl or tolylisocyanate, diisocyanates such as hexamethylene diisocyanate, tolylene diisocyanate, isophorone diisocyanate, xylylene diisocyanate, methylenebis(4-phenyleneisocyanate), and polyarylpolyisocyanates such as dimethylenetriphenylene triisocyanate. Other isocyanates which can be used in preparing the oxazolidinones include carbamate or urylene group-containing adducts of diisocyanates and diols or polyols. Suitable A groups include, for example, C$_6$H$_5$—, CH$_3$C$_6$H$_4$—, —C$_6$H$_3$(CH$_3$)—, —CH$_2$C$_6$H$_4$CH$_2$—, —C$_6$H$_4$CH$_2$C$_6$H$_4$—, —(CH$_2$)$_6$—, —(CH$_2$)$_6$N[CONH(CH$_2$)$_6$]$_2$, C$_8$F$_{17}$SO$_3$C$_6$H$_4$—, —C$_6$H$_{10}$CH$_2$C$_6$H$_{10}$—, C$_8$F$_{17}$SO$_2$N[C$_2$H$_4$OCONHC$_6$H$_3$(CH$_3$)—]$_2$, and —C$_6$H$_4$CH$_2$C$_6$H$_3$(—)CH$_2$C$_6$H$_4$—.

In each of the above fluorochemical oxazolidones of general Formula I where there are a plurality of $R^1$, $R^2$ and A groups or moieties, each can be the same or different. Also Formula I represents individual compounds or mixtures of compounds, for example, as they are obtained as products from reactions used in their preparation. In addition, small amounts of by-products, with and without the fluoroaliphatic radical $R_f$, and not represented by Formula I, can also be present in small amounts in said mixtures or reaction products because of the reaction conditions involved in their preparation. The presence of such small amounts of by-products, generally less than 10 weight percent, does not affect the usefulness of the fluorochemical oxazolidinone mixtures or compounds of this invention.

The fluoroaliphatic radical, $R_f$, is a fluorinated, stable, inert, non-polar, preferably saturated, monovalent moiety which is both oleophobic and hydrophobic. It can be straight chain, branched chain, or, if sufficiently large, cyclic, or combinations thereof, such as alkylcycloaliphatic radicals. The skeletal chain in the fluoroaliphatic radical can include catenary oxygen, hexavalent sulfur, and/or trivalent nitrogen hetero atoms bonded only to carbon atoms of the skeletal chain, such hetero atoms providing stable linkages between fluorocarbon portions of $R_f$ and not interfering with the inert character of the $R_f$ radical. While $R_f$ can have a large number of carbon atoms, compounds where $R_f$ is not more than 20 carbon atoms will be adequate and preferred since large radicals usually represent a less efficient utilization of fluorine than is possible with smaller $R_f$ radicals. Generally $R_f$ will have 3 to 20 carbon atoms, preferably 6 to about 12, and will contain 40 to 78 weight percent, preferably 50 to 78 weight percent, fluorine. The terminal portion of the $R_f$ group preferably has at least three fully fluorinated carbon atoms, e.g., CF$_3$CF$_2$CF$_2$—, and the preferred compounds are those in which the $R_f$ group is fully or substantially completely fluorinated, as in the case where $R_f$ is perfluoroalkyl, e.g., CF$_3$(CF$_2$)$_n$—.

When the $R^1$ or $R^2$ groups contain a fluoroaliphatic radical, $R_f$, the fluoroaliphatic radical is bonded to the 5-position carbon atom of the oxazolidinone moiety by linking group, Q. Each Q can comprise a hetero atom-containing group, e.g., a group containing —S—, —O—, and/or

or an organic group or a combination of such groups, examples of which are polyvalent aliphatic, i.e., —CH$_2$—, —CH$_2$CH$_2$—, and —CH$_2$CH(CH$_2$—)$_2$, —SO$_2$N(CH$_2$—)$_2$, polyvalent aromatic, oxy, thio, carbonyl, sulfone, sulfoxy, —N(CH$_3$)-, sulfonamido, carbonamido, sulfonamidoalkylene, e.g., —SO$_2$NR$^4$(CH$_2$)$_3$, where e is 1 to 6 and R$^4$ is lower alkyl having 1 to 4 carbon atoms, carbonamidoalkylene, carbonyloxy, urethane, e.g., —CH$_2$CH$_2$OCONH—, and urylene, e.g., —NHCONH—. The linkage Q for a specific fluorochemical oxazolidinone will be dictated by the ease of preparation of such a compound and the availability of necessary precursors thereof. However, the Q group is preferably free of said active hydrogen atoms.

Generally, the fluorochemical oxazolidinone compositions of this invention will contain about 20 to 70 weight percent, preferably about 25 to 50 weight percent, of carbon-bonded fluorine. If the fluorine content is less than about 20 weight percent, an impractically large amount of the fluorochemical oxazolidinone compositions will generally be required, while fluorine contents greater than about 70 weight percent are unnecessary to achieve the desired surface properties and thus represent an uneconomical use of fluorine.

The fluorochemical oxazolidinone compositions of this invention can be prepared using known organic reactions e.g., from the reaction of epoxides or halohydrin, e.g., chlorohydrins or bromohydrins, with organic isocyanates in each which reaction at least one of the reactants contains an $R_f$ radical.

The reactions may be carried out stepwise by reacting the halohydrin with the isocyanate under urethane bond forming conditions, e.g. 20° C. to 100° C. for about 1 to 24 hours, to form a urethane intermediate, followed by addition of a base and reaction at about 20° C. to 100° C. for about 1 to 24 hours to form the oxazolidinone compositions. Alternatively, an epoxide can be reacted with an isocyanate in the presence of a catalyst, such as diethyl zinc, to form the oxazolidinone directly.

Representative reaction schemes for the preparation of the fluorochemical oxazolidinone compositions of this invention are outlined below. In these schemes, R is methyl or lower alkyl, e.g., having 1 to 18 carbon atoms, and $R_f$ and A are as defined hereinabove.

Scheme I $R_fSO_2N(R)H + CH_2CHCH_2Cl \longrightarrow$

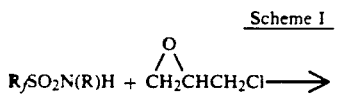

$R_fSO_2N(R)CH_2CH(CH_2Cl)OH + A-NCO \longrightarrow$ $R_fSO_2N(R)CH_2CH(CH_2Cl)OCONH-A \xrightarrow{KOH}$

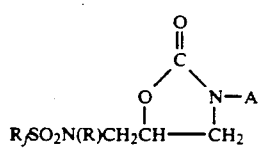

Scheme II $2\ R_fSO_2N(R)CH_2CH(CH_2Cl)OH + A(NCO)_2 \longrightarrow$ $[R_fSO_2N(R)CH_2CH(CH_2Cl)OCONH]_2A \xrightarrow{NaOCH_3}$

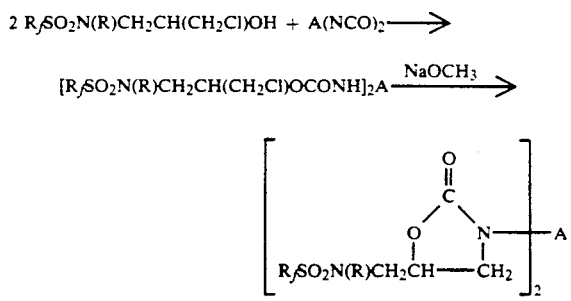

Scheme III

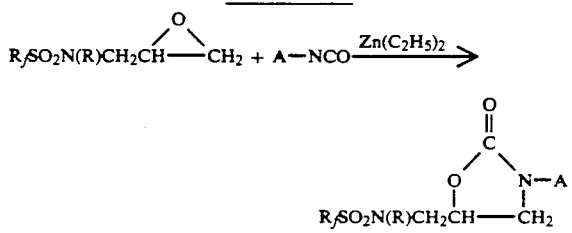

Scheme IV

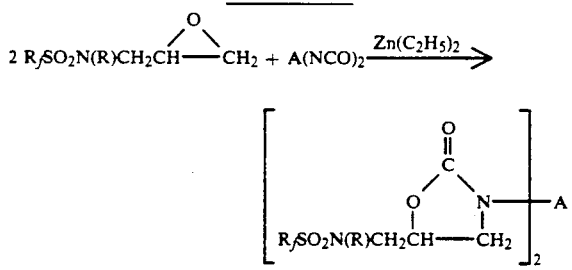

Scheme V $R'OH + A-NCO \longrightarrow R'OCONH-A$

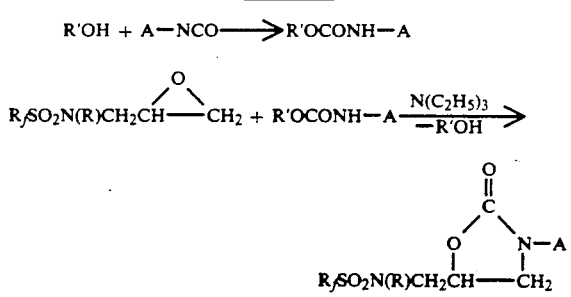

Scheme VI $2\ R_fSO_2N[CH_2CH(CH_2Cl)OH]_2 + 2\ C_6H_5OCH_2CH(CH_2Cl)OH + 3\ A(NCO)_2 \longrightarrow$

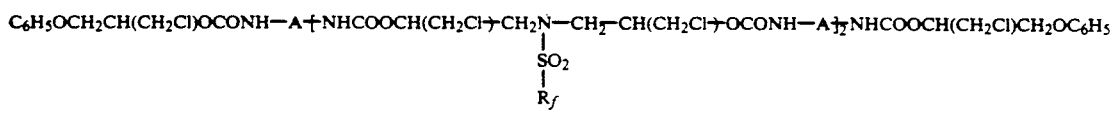

-continued
Scheme VI

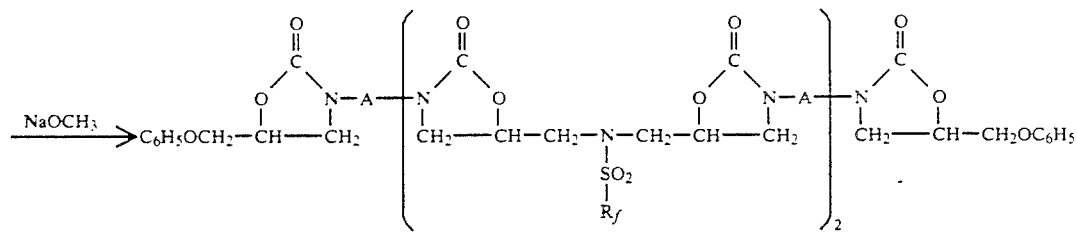

Scheme VII

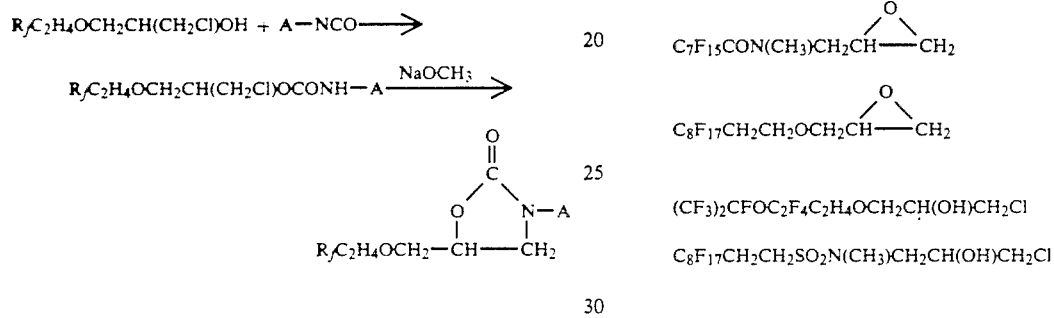

Scheme VIII

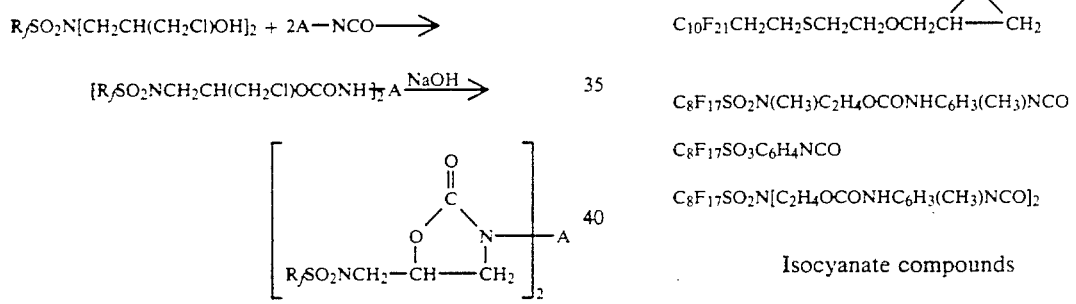

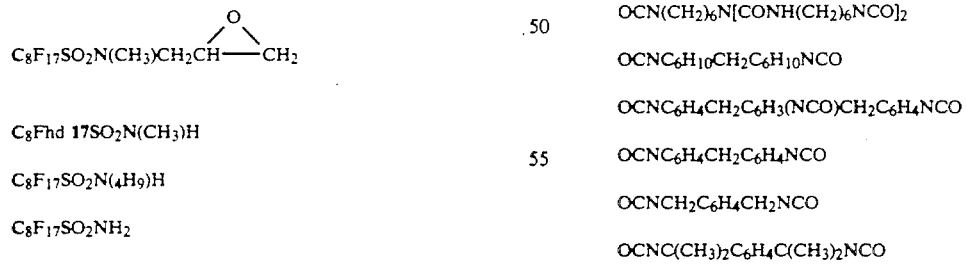

Useful reactants for the synthesis of the fluorochemical oxazolidinones of this invention include:

Fluorochemical compounds

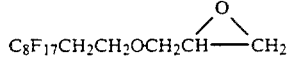

C$_8$F$_{17}$SO$_2$N(CH$_3$)H

C$_8$F$_{17}$SO$_2$N($_4$H$_9$)H

C$_8$F$_{17}$SO$_2$NH$_2$

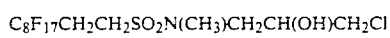

C$_6$F$_{13}$SO$_2$N(C$_2$H$_5$)CH$_2$CH(OH)CH$_2$Cl

C$_8$F$_{17}$CH$_2$CH$_2$OCH$_2$CH(OH)CH$_2$Cl

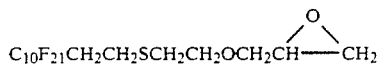

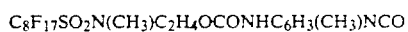

(CF$_3$)$_2$CFOC$_2$F$_4$C$_2$H$_4$OCH$_2$CH(OH)CH$_2$Cl

C$_8$F$_{17}$CH$_2$CH$_2$SO$_2$N(CH$_3$)CH$_2$CH(OH)CH$_2$Cl

C$_8$F$_{17}$SO$_2$N(CH$_3$)C$_2$H$_4$OCONHC$_6$H$_3$(CH$_3$)NCO

C$_8$F$_{17}$SO$_3$C$_6$H$_4$NCO

C$_8$F$_{17}$SO$_2$N[C$_2$H$_4$OCONHC$_6$H$_3$(CH$_3$)NCO]$_2$

Isocyanate compounds

C$_6$H$_5$NCO

CH$_3$C$_6$H$_4$NCO

OCN(CH$_2$)$_6$NCO

OCN(CH$_2$)$_6$N[CONH(CH$_2$)$_6$NCO]$_2$

OCNC$_6$H$_{10}$CH$_2$C$_6$H$_{10}$NCO

OCNC$_6$H$_4$CH$_2$C$_6$H$_3$(NCO)CH$_2$C$_6$H$_4$NCO

OCNC$_6$H$_4$CH$_2$C$_6$H$_4$NCO

OCNCH$_2$C$_6$H$_4$CH$_2$NCO

OCNC(CH$_3$)$_2$C$_6$H$_4$C(CH$_3$)$_2$NCO

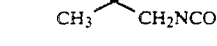

Epoxy compounds

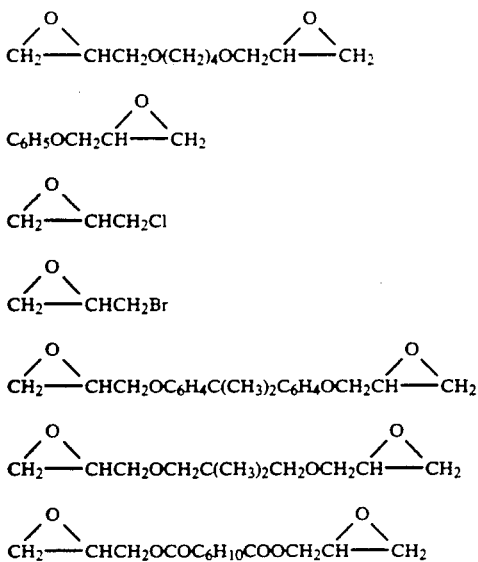

The fluorochemical oxazolidinone compositions of this invention are particularly useful as additives in synthetic organic polymer melts. Synthetic polymeric fibers and films, extruded from melts to which the fluorochemical oxazolidinones of this invention have been incorporated, have low surface energy, oil and water repellency and resistance to soiling. Such polymers include synthetic linear polyamides, e.g. nylon-6 and nylon-66, polyester, e.g. polyethylene terephthalate, and polyolefin, e.g., polyethylene and polypropylene. The fibers and films of this invention can be made by preparing a blend of the solid fluorochemical oxazolidinone composition with the solid synthetic polymer, by intimately mixing the solid fluorochemical with pelletized or powdered polymer, and melt extruding the blend into fibers or films by known methods. The fluorochemical oxazolidinone composition can be mixed per se with the polymer or the fluorochemical oxazolidinone composition can be mixed with the polymer in the form of a "masterbatch" (concentrate) of the fluorochemical in the polymer. Also, an organic solution of the fluorochemical oxazolidinone composition may be mixed with the powdered or pelletized polymer, the mixture dried to remove solvent, then melted and extruded. Alternatively, molten fluorochemical oxazolidinone (as a compound(s) or a masterbatch) can be injected into a molten polymer stream to form a blend just prior to extrusion into fibers or films.

In addition to the use of the fluorochemical oxazolidinone compositions of this invention in modifying the properties of fibers, e.g., carpet fibers, as described above, they are also useful as blend additives in blown microfibers for use in making non-woven fabrics having low surface energy, oil and water repellency and/or soiling resistance.

The amount of fluorochemical oxazolidinone composition of this invention used as melt additives is that amount sufficient to achieve the desired properties of oil and water repellency and/or soiling resistance as well as reduced surface energy. Preferably, the amount of fluorochemical to be used will be that amount which provides from about 100 to 10,000 ppm fluorine, more preferably 200 to 5000 ppm most preferably 400 to 3000 ppm fluorine, based on the weight of the fiber or film, in the fiber or film after extrusion.

After melt extrusion of the fiber or film an annealing step is generally carried out to enhance surface energy lowering and oil and water repellency for a particular fluorochemical oxazolidinone additive. This annealing process is conducted below the melt temperature of the synthetic polymer, for example, in the case of nylon, at about 150 to 220° C for a period of about 30 seconds to 5 minutes. In some cases, the presence of moisture, e.g., by using an autoclave to anneal, can improve the effectiveness of the fluorochemical.

The fluorochemical oxazolidinone composition of this invention can also be employed as aqueous suspensions or emulsions, or as organic solvent solutions, in the treatment of textile fibers (or filaments) during their manufacture, e.g. in combination with spin finishes, or in the treatment of porous or fibrous substrates such as textiles, carpets, paper and leather, to impart oil and water repellency and anti-soiling properties thereto. The fibers or filaments as such or in an aggregated form, e.g., yarn, tow, web, or roving, or the fabricated textile, e.g., articles such as carpet and woven fabrics, can be treated with the fluorochemical oxazolidinone compositions. The treatment can be carried out by applying the fluorochemical oxazolidinone compositions as organic solutions or aqueous or organic dispersions by known techniques customarily used in applying fluorochemicals, e.g., fluorochemical acrylate copolymers, to fibers and fibrous substrates. For example, the fluorochemical treatment, with the fluorochemical being in the form of an aqueous emulsion or organic solution, can be carried out by immersing the fibrous substrates in a bath containing the cationic fluorochemical blends, padding the substrate or spraying the same with the fluorochemical emulsions or solutions, or by foam, kiss-roll, or metering applications e.g., spin finishing, and then drying the treated substrates if solvent is present. If desired, the fluorochemical composition or blends can be co-applied with conventional fiber treating agents, e.g., antistatic agents or non-aqueous fiber lubricants.

The fluorochemical oxazolidinones of this invention can also be used as additives to polymer coatings and articles, e.g., to improve water resistance, lower surface energy, improve dielectric properties, etc. Such polymers include both thermoset resins and thermoplastic polymers such as epoxies, urethanes, acrylics, polystyrene, etc.

The fluorochemical oxazolidinones of this invention can also be used as blends with other fluorochemicals, e.g., with fluorochemical poly(oxyalkylene) compounds, oligomers or polymers.

The following nonlimiting examples are presented to further describe and illustrate the invention.

Example 1

In a 1 liter, 3-neck reaction flask fitted with a mechanical stirrer, condenser, gas inlet tube, thermometer, addition funnel and electric heating mantle were placed 47.0 g (0.25 mole) m-xylylene diisocyanate, 50 g ethyl acetate solvent and 6 drops of dibutyl tin dilaurate catalyst. To this stirred mixture heated to 75° C. was added over a period of 2.5 hours under a slow nitrogen purge, a 50 weight percent ethyl acetate solution containing 297 g (0.5 mole) of $C_8F_{17}SO_2N(CH_3)CH_2CH(OH)CH_2Cl$ prepared from $C_8F_{17}SO_2N(CH_3)H$ and epichlorohydrin. Heating and stirring were continued for an additional 4 hours until substantially all of the isocyanate groups had been converted to urethane groups as determined by infrared absorption analysis. To this reaction mixture, cooled to room temperature (about 20° C.) and containing mainly the intermediate urethane product,

[C$_8$F$_{17}$SO$_2$N(CH$_3$)CH$_2$CH(CH$_2$C-l)OCONHCH$_2$]$_2$C$_6$H$_4$ was added with stirring a solution of 27.0 g (0.5 mole) of NaOCH$_3$ in 81 g methanol to effect cyclization of the urethane group and thereby formation of the oxazolidinone. The reaction mixture exothermed to 50° C. and this temperature was maintained with stirring for 5.5 hours. The reaction mixture was cooled to about 20° C., and the white solid product which formed during the course of the reaction was collected by filtration, washed once with 100 g ethyl acetate, twice with 100 g portions of deionized water and finally dried under water aspirator vacuum at 60° C. for 16 hours. Infrared and proton nmr analyses confirmed the product to be a fluorochemical 2-oxazolidinone having the structure

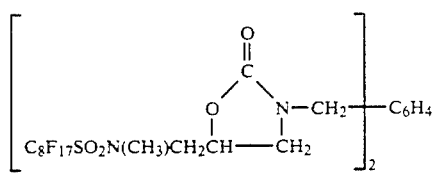

EXAMPLES 2-14

Following the general procedure of Example 1, various organic alcohols and isocyanates, as set forth in Table 1, were reacted to produce the fluorochemical oxazolidinones of the present invention set forth in Table 2. The bases used to effect cyclization of the urethane to form the oxazolidinone are also set forth in Table 1.

TABLE 1

| Ex. | Alcohol(s) | Isocyanate | Base |
|---|---|---|---|
| 1 | C$_8$F$_{17}$SO$_2$N(CH$_3$)CH$_2$CH(CH$_2$Cl)OH | OCNCH$_2$—C$_6$H$_4$—CH$_2$NCO | NaOCH$_3$ |
| 2 | C$_8$F$_{17}$SO$_2$N(CH$_3$)CH$_2$CH(CH$_2$Cl)OH | OCN—C$_6$H$_3$(CH$_3$)—NCO (2,4-tolylene diisocyanate) | NaOCH$_3$ |
| 3 | C$_8$F$_{17}$SO$_2$N(CH$_3$)CH$_2$CH(CH$_2$Cl)OH | OCN—C$_6$H$_4$—CH$_2$—C$_6$H$_4$—NCO | NaOCH$_3$ |
| 4 | C$_8$F$_{17}$SO$_2$N(CH$_3$)CH$_2$CH(CH$_2$Cl)OH | OCN—C$_6$H$_5$ | KOH |
| 5 | C$_8$F$_{17}$SO$_2$N(CH$_3$)CH$_2$CH(CH$_2$Cl)OH | OCN—(CH$_2$)$_6$—NCO | NaOCH$_3$ |
| 6 | C$_8$F$_{17}$SO$_2$N(CH$_3$)CH$_2$CH(CH$_2$Cl)OH | OCN—C(CH$_3$)$_2$—C$_6$H$_4$—C(CH$_3$)$_2$—NCO | NaOCH$_3$ |
| 7 | C$_8$F$_{17}$SO$_2$N(CH$_3$)CH$_2$CH(CH$_2$Cl)OH | OCN—C$_6$H$_3$(CH$_3$)$_2$—C(CH$_3$)$_2$CH$_2$NCO | NaOCH$_3$ |
| 8 | C$_8$F$_{17}$SO$_2$N(CH$_3$)CH$_2$CH(CH$_2$Cl)OH | OCN—C$_6$H$_{10}$—CH$_2$—C$_6$H$_{10}$—NCO | NaOCH$_3$ |
| 9 | C$_8$F$_{17}$SO$_2$N(CH$_3$)CH$_2$CH(CH$_2$Cl)OH | OCN(CH$_2$)$_6$N[CONH(CH$_2$)$_6$NCO]$_2$ | NaOCH$_3$ |

TABLE 1-continued

| Ex. | Alcohol(s) | Isocyanate | Base |
|---|---|---|---|
| 10 | $C_8F_{17}SO_2N(CH_3)CH_2CH(CH_2Cl)OH$ | OCN—C₆H₄—CH₂—C₆H₃(NCO)—CH₂—C₆H₄—NCO (1,3,5-trisubstituted central ring) | $NaOCH_3$ |
| 11 | $C_8F_{17}C_2H_4OCH_2CH(CH_2Cl)OH$ | OCN—C₆H₃(CH₃)—NCO (toluene diisocyanate) | $NaOCH_3$ |
| 12 | $C_8F_{17}SO_2N(CH_3)CH_2CH(CH_2Cl)OH$ and $C_8F_{17}OCH_2CH(CH_2Cl)OH$ | $OCNCH_2$—C₆H₄—$CH_2NCO$ | $NaOCH_3$ |
| 13 | $C_8F_{17}SO_2N[CH_2CH(CH_2Cl)OH]_2$ | OCN—C₆H₅ | KOH |
| 14 | $C_8F_{17}SO_2N(CH_3)CH_2CH(CH_2Cl)OH$ and $C_8F_{17}SO_2N[CH_2CH(CH_2Cl)OH]_2$ | $OCNCH_2$—C₆H₄—$CH_2NCO$ | $NaOCH_3$ |

TABLE 2

| Ex. | Fluorochemical Oxazolidinone |
|---|---|
| 1 | $C_8F_{17}SO_2N(CH_3)CH_2$—CH—CH₂—N(C=O)—O— (oxazolidinone)—$CH_2$—C₆H₄—$CH_2$—N(C=O)—O—CH₂—CH—$CH_2N(CH_3)SO_2C_8F_{17}$ |
| 2 | Bis-oxazolidinone linked through a toluene (CH₃-substituted phenylene) ring; end groups $C_8F_{17}SO_2N(CH_3)CH_2$—CH—CH₂— and —CH₂—CH—$CH_2N(CH_3)SO_2C_8F_{17}$ |
| 3 | Bis-oxazolidinone linked through —C₆H₄—CH₂—C₆H₄— (methylenediphenylene); end groups $C_8F_{17}SO_2N(CH_3)CH_2$—CH—CH₂— and —CH₂—CH—$CH_2N(CH_3)SO_2C_8F_{17}$ |
| 4 | $C_8F_{17}SO_2N(CH_3)CH_2$—CH—CH₂—N(C=O)—O— (oxazolidinone)—C₆H₅ |
| 5 | Bis-oxazolidinone linked through —(CH₂)₆—; end groups $C_8F_{17}SO_2N(CH_3)CH_2$—CH—CH₂— and —CH₂—CH—$CH_2N(CH_3)SO_2C_8F_{17}$ |

TABLE 2-continued
| Ex | Fluorochemical Oxazolidinone |
|---|---|
| 6 | 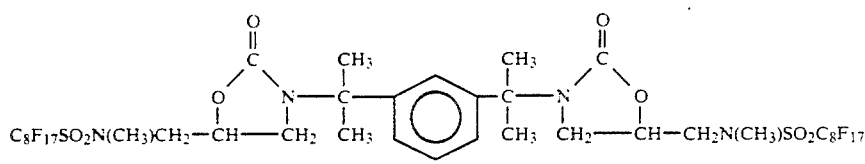 |
| 7 | 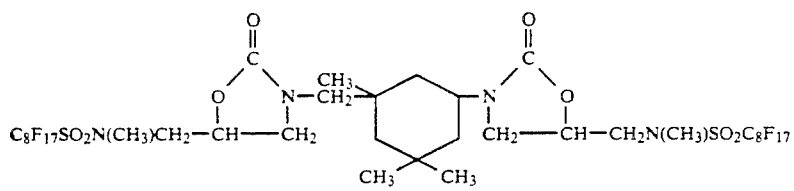 |
| 8 | 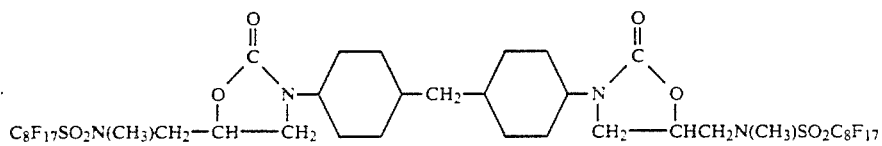 |
| 9 | 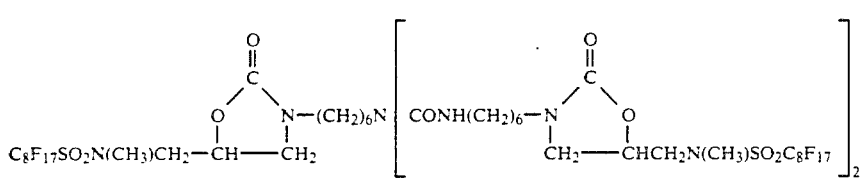 |
| 10 | 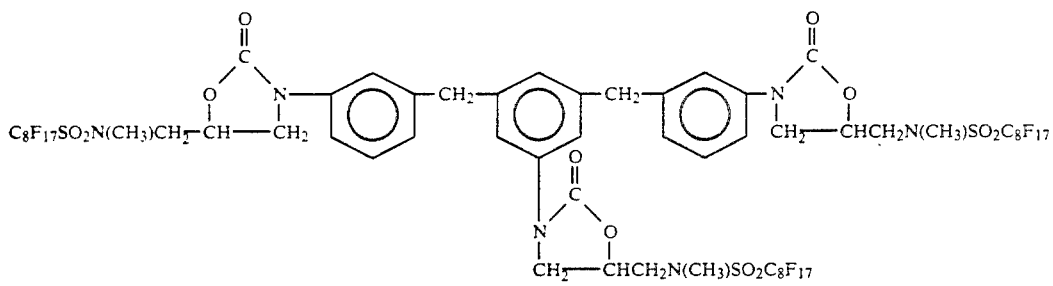 |
| 11 | 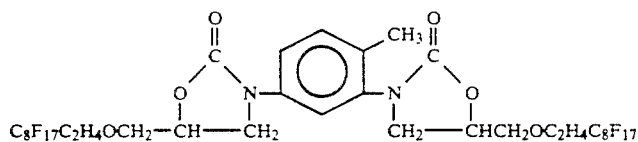 |
| 12 | 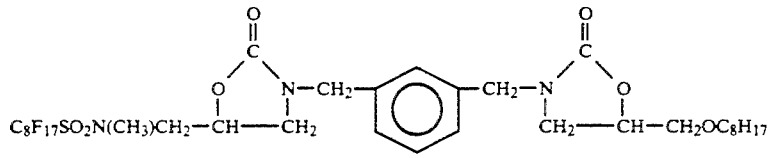 |
| 13 | 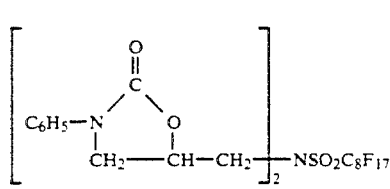 |

TABLE 2-continued

| Ex. | Fluorochemical Oxazolidinone |
|---|---|
| 14 | 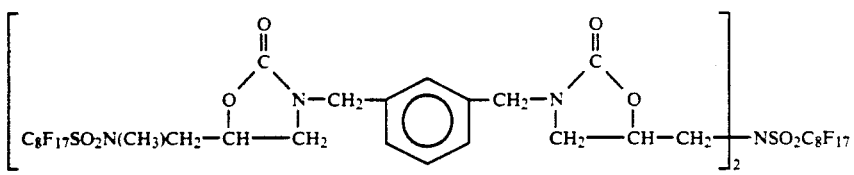 |

In the examples hereinbelow, the following test procedures were used:

Water Repellency (WR) Test. The aqueous stain or water repellency of treated samples is measured using a water/isopropyl alcohol test, and is expressed in terms of a water repellency rating of the treated carpet or fabric. Treated carpets which are penetrated by or resistant only to a 100 percent water/0 percent isopropyl alcohol mixture (the least penetrating of the test mixtures) are given a rating of 0, (representing the amount of isopropyl alcohol present) whereas treated fabrics resistant to a 0 percent water/100 percent isopropyl alcohol mixture (the most penetrating of the test mixtures) are given a rating of 10. Other intermediate values are determined by use of other water/isopropyl alcohol mixtures. The water repellency rating corresponds to the most penetrating mixture which does not penetrate or wet the fabric after 10 seconds contact. In general a water repellency rating of 1 (90% water/10% isopropyl alcohol) or better, e.g., 2 (80% water/20% isopropyl alcohol) is desirable for carpet.

Oil Repellency (OR) Test. The oil repellency of treated carpet and textile samples is measured by AATCC Standard Test 118-1978, which test is based on the resistance of treated fabric to penetration by oils of varying surface tensions. Treated fabrics resistant only to Nujol TM, and the least penetrating of the test oils, are given a rating of 1, whereas treated fabrics resistant to heptane (the most penetrating of the test oils) are given a value of 8. Other intermediate values are determined by use of other pure oils or mixtures of oils. The rated oil repellency corresponds to the most penetrating oil (or mixture of oils) which does not penetrate or wet the fabric after 10 seconds contact rather than the 30 seconds contact of the Standard Test. Higher number indicate better oil repellency. In general, an oil repellency of 2 or greater is desirable for fabric.

Walk-On-Soiling (WOS) Test. The soil resistance of treated and untreated carpet was determined by exposure to pedestrian traffic according to AATCC Test method 122-1979. The exposure site was the corridor (hallway) in a heavily travelled industrial building for an exposure of about 10,000 "traffics" (or one "WOS cycle"). The samples are repositioned periodically to insure uniform exposure and are vacuumed every 24 hours during the test which takes 4 working days. After each WOS exposure cycle, i.e. 10,000 "traffics", and before visual evaluation, the carpet samples were vacuumed then subjected to steam cleaning (SC) using a Mr. Clean TM carpet steam cleaning machine employing an aqueous cleaning solution prepared from a solution of 4 ounces of Hoover carpet emulsifier in 1 gallon of 49° C. water, passing the machine over the carpet squares first in one direction then once at right angles. The samples were rinsed, using tap water in the steam cleaning machine, then allowed to dry overnight and visually evaluated for degree of soiling as compared to an untreated carpet sample. After rating, additional soiling cycles and ratings were generally done on each carpet sample, including in each case a WOS cycle, vacuuming, steam cleaning, drying and visual rating.

| WOS Rating* | Description |
|---|---|
| 0 | equal to control |
| ±2 | slightly better (+) or worse (−) than control |
| ±4 | significant difference compared to control |
| ±6 | very significant difference compared to control |

*Grey scale values multiplied by 4.

Rating values vary from −6 to +6 as described, minus (−) values indicating greater soiling than the control, and positive (+) values indicating less soiling than the control, and 0 indicating the same soiling as the control. Surface Energy (fiber). Surface energy determinations for fibers are made using the contact-angle method set forth in "A Simple Apparatus and Technique for Contact-Angle Measurement on Small-Denier Single Fibers," *Textile Research Journal*, vol. 39, pp 958-962 (1969). Surface Energy (film). Surface energy determination for films are made using the contact-angle method set forth in "Estimation of the Surface Free Energy of Polymers", *Journal of Applied Polymer Science*, vol. 13, pp. 174-177 (1969) using Lubinol TM mineral oil (available from Purepac Pharmaceutical Co., a division of Kalipharma, Inc.) and glycerine. 180° Peel Adhesion. A 1-inch wide strip of pressure-sensitive adhesive tape (Type SCTT-100, available from 3M Company) is adhered to the outside portion of the film under the weight of a 4.5 lb (2 kg) hard rubber roller, 2 passes in each direction. The tape is peeled from the film at 180° at a rate of 30.5 cm/min. Testing is done initially, after 1 day adherence, and after 7 days adherence at room temperature. Tape Bond. A ½-inch wide strip of Scotch ® brand No. 898 filament tape is adhered to the outside portion of the film under the weight of a 4.5 lb (2 kg) hard rubber roller, 2 passes in each direction. The tape is peeled from the film at 180° at a rate of 25.4 cm/min. immediately after adherence.

EXAMPLES 15-22

Fluorochemical oxazolidinones (FC) of Table 2 (compound no. corresponding to example no.) were dry mixed with dried (105° C. overnight) nylon 66 pellets at various concentration levels and the mixture was melt extruded at a die temperature of 280° C. into 2100 denier/110 filament yarn using a draw ratio of 3.5. The yarn was then tufted into carpet.

The carpet was mock dyed at a 30:1 liquor ratio using an aqueous bath containing 1 weight percent Alkanol TM ND, a leveling agent available from DuPont & Co. and 2 weight percent ammonium sulfate to give a pH of 6.5. The mock-dyed carpet was rinsed with water, spun dry, blotted to remove excess water, and dried at 70° C. for 20 minutes. Fluorine analysis of the carpet fibers, where evaluated, is shown in Table 3. The mock-dyed carpet was mounted on boards, and the mounted carpet samples were heat-set in an oven at 190° C. for 90 seconds.

The mounted carpet was tested for Walk-On-Soiling (WOS) after one soiling cycle and after additional soiling cycles, with the number of soiling cycles in parentheses after the rating. The results are set forth in Table 3.

TABLE 3

| Ex. No. | Compound | F content Wt. % | F content in melt (ppm) | Fluorine content in carpet Before dyeing (ppm) | Fluorine content in carpet After dyeing (ppm) | Retention in fiber (%) | WOS rating |
|---|---|---|---|---|---|---|---|
| 15 | 1 | 0.25 | 1218 | 988 | 800 | 81 | 0(1) 0(3) |
| 16 | 1 | 0.50 | 2435 | 1990 | 1990 | 100 | 1(1) 0(2) |
| 17 | 1 | 1.0 | 4870 | 3500 | 3500 | 100 | 6(1) 5(3) 4(5) |
| 18 | 2 | 0.25 | 1230 | —* | 655 | —* | −2(1) 2(4) |
| 19 | 2 | 0.50 | 2460 | 1293 | 957 | 74 | 0(1) 2(3) |
| 20 | 2 | 1.0 | 4920 | 3106 | 2702 | 87 | 0(1) 1(4) |
| 21 | 3 | 0.5 | 2325 | 1604 | 1187 | 74 | 0(1) 3(3) |
| 22 | 3 | 1.0 | 4650 | 3239 | 2818 | 87 | 0(1) 2(4) |

*not tested

EXAMPLES 23-28

Fluorochemical oxazolidinones (FC) of Table 2 (compound no. corresponding to example no.) were dry mixed with dried (105° C. overnight) nylon 66 pellets at various concentration levels and the mixture was melt extruded at a die temperature of 280° C. into 2100 denier/110 filament yarn using a draw ratio of 3.5. The yarn was then tufted into carpet.

The carpet was mock dyed at a 30:1 liquor ratio using an aqueous bath containing 1 weight percent Al-kanol ™ ND, a leveling agent available from DuPont, and 2 weight percent ammonium sulfate to give a pH of 6.5. The mock-dyed carpet was rinsed with water, spun dry, blotted to remove excess water, and dried at 70° C. for 20 minutes. The mock-dyed carpet was mounted on boards, and the mounted carpet samples were heat-set in an oven at 190° C. for 90 seconds.

The mounted carpet was tested for Walk-On-Soiling (WOS) after one soiling cycle and after additional soiling cycles, with the number of soiling cycles in parentheses after the rating. The results are set forth in Table 4.

TABLE 4

| Ex. No. | Compound | F content Wt. % | F content in melt (ppm) | WOS rating |
|---|---|---|---|---|
| 23 | 5 | 0.5 | 2475 | 0(1) 1(6) |
| 24 | 5 | 1.0 | 4950 | 2(1) 2(4) |
| 25 | 6 | 0.25 | 1170 | 1(1) 2(4) |
| 26 | 8 | 0.5 | 2315 | 0(1) 2(3) |
| 27 | 9 | 0.5 | 2215 | 1(1) 2(2) |
| 28 | 10 | 0.25 | 1160 | 0(1) 1(3) |

EXAMPLES 29-43

Nylon 6 filament yarn containing fluorochemical oxazolidinones of Table 2 (compound no. corresponding to example no.) were prepared by melt extrusion as in Examples 15-22 except that the die temperature was 270° C. and the yarn was about 1100 denier/68 filament yarn. The yarn was then tufted into carpet. The carpet was dyed with a yellow dye using either a beck or continuous dyeing process as indicated. Samples were tested for walk-on-soiling as in Examples 15-22 after dyeing for beck and continuous dyed samples and after dyeing and additionally heat setting at 190° C. for 90 seconds for beck dyed samples. Results are set forth in Table 5 (Examples 29-38) for beck dyed carpet and in Table 6 (Examples 39-43) for continuous dyed carpet.

TABLE 5

| Ex. No. | Compound | F Content in melt (ppm) | F content (ppm) in carpet after dyeing and indicated no. of WOS cycles | | | WOS rating after indicated number of cycles Dyed | | | | | Dyed and heat set | | | | |
|---|---|---|---|---|---|---|---|---|---|---|---|---|---|---|---|
| | | | 0 | 1 | 2 | 1 | 2 | 3 | 4 | 5 | 1 | 2 | 3 | 4 | 5 |
| 29 | 1 | 2500 | 1761 | 1662 | 1877 | 6 | 1 | 0 | 0 | 1 | | | | | |
| 30 | 1 | 2500 | 1805 | 1699 | 1802 | | | | | | 1 | 1 | 2 | 1 | 1 |
| 31 | 5 | 2500 | 1609 | 1649 | 1290 | 0 | 0 | 0 | 0 | 0 | | | | | |
| 32 | 5 | 2500 | 1769 | 1767 | 1775 | | | | | | 0 | 1 | 2 | 2 | 0 |
| 33 | 6 | 2500 | 1658 | 1682 | 1766 | 2 | 1 | 0 | −1 | −2 | | | | | |
| 34 | 6 | 2500 | 1739 | 1681 | 1769 | | | | | | 0 | 2 | 1 | 1 | 1 |
| 35 | 9 | 2500 | 1152 | 1136 | 1188 | 2 | 1 | 0 | 0 | −2 | | | | | |
| 36 | 9 | 2500 | 1212 | 1152 | 1204 | | | | | | 0 | 2 | 1 | 1 | 0 |
| 37 | 10 | 2500 | 1748 | 1662 | 1981 | 4 | 1 | −1 | 1 | 1 | | | | | |
| 38 | 10 | 2500 | 1834 | 1847 | 1827 | | | | | | 0 | 2 | 1 | 0 | 0 |

TABLE 6

| Ex. No. | Compound | F Content in melt (ppm) | F content (ppm) in carpet after dyeing and indicated no. of WOS cycles | | | WOS rating after indicated number of WOS cycles | | | | |
|---|---|---|---|---|---|---|---|---|---|---|
| | | | 0 | 1 | 2 | 1 | 2 | 3 | 4 | 5 |
| 39 | 1 | 2500 | 1814 | 1689 | 1891 | 4 | 4 | 2 | 2 | 0 |
| 40 | 5 | 2500 | 1614 | 1749 | 1718 | 1 | 0 | 1 | 1 | 1 |
| 41 | 6 | 2500 | 1601 | 1705 | 1673 | 3 | 1 | 0 | 0 | 0 |

TABLE 6-continued

| Ex. No. | Compound | F Content in melt (ppm) | F content (ppm) in carpet after dyeing and indicated no. of WOS cycles | | | WOS rating after indicated number of WOS cycles | | | | |
|---|---|---|---|---|---|---|---|---|---|---|
| | | | 0 | 1 | 2 | 1 | 2 | 3 | 4 | 5 |
| 42 | 9 | 2500 | 1131 | 1195 | 1153 | 0 | 0 | −1 | 0 | −1 |
| 43 | 10 | 2500 | 1855 | 1932 | 1763 | 1 | 1 | 1 | 1 | 0 |

EXAMPLES 44–49, AND COMPARATIVE EXAMPLES 1 and 2

In Examples 44–49, nylon 66 carpet yarn containing 3500 ppm of the fluorochemical oxazolidinone of Example 1 was spun into yarn as in Example 15–28 having the size indicated in Table 7. In comparative Examples 1 and 2 nylon 66 containing no fluorochemical oxazolidinone was spun into about 2100 denier/110 filament yarn. The yarns were tufted into carpet. Samples were annealed in an autoclave at 125° C. for the times indicated in Table 6 and were tested for oil repellency (OR), water repellency (WR), and surface energy (SE), the results being shown in Table 7.

TABLE 7

| Example | Yarn Size (den/fil) | Annealing time (min) | OR | WR | SE (dynes/cm) |
|---|---|---|---|---|---|
| 44 | 1300/110 | 5 | 0 | 3 | —* |
| 45 | 1300/110 | 10 | 2 | 3 | —* |
| 46 | 1300/110 | 15 | 3 | 4 | 13 |
| 47 | 2100/110 | 5 | 0 | 3 | —* |
| 48 | 2100/110 | 10 | 3 | 4 | —* |
| 49 | 2100/110 | 15 | 4 | 4 | 13 |
| Comp 1 | 2100/110 | 5 | 0 | 3 | —* |
| Comp 2 | 2100/110 | 15 | 0 | 2 | 34 |

*not tested

EXAMPLES 50–55 AND COMPARATIVE EXAMPLE 3-5.

In Examples 50–55, nylon 6 1100 denier/68 filament carpet yarn was prepared as described in Examples 29–43, except that Examples 50–52 contained the fluorochemical oxazolidinone of Example 1 and Examples 53–55 contained the fluorochemical oxazolidinone of Example 6 in the concentration shown in Table 8. In Comparative Examples 3-5 nylon 6 carpet yarn containing no fluorochemical oxazolidinone was spun into 1100 denier/68 filament yarn. The yarns were knit into about 5 cm diameter tubes and dyed as in Examples 29–38. The tubes of Example 51, 54 and Comparative Example 4 were then heat-set for 90 seconds at 190° C. The tubes of Examples 52, 55 and Comparative Example 5 were heat-set for 5 minutes at 160° C. after dyeing. The tubes were tested for oil repellency (OR) and water repellency (WR), the results being shown in Table 8.

TABLE 8

| Example | F content (ppm) | OR | WR |
|---|---|---|---|
| 50 | 1900 | 1 | 3 |
| 51 | 2200 | 5 | 4 |
| 52 | 1950 | 5 | 5 |
| 53 | 1950 | 0 | 1 |
| 54 | 1800 | 2 | 3 |
| 55 | 1750 | 3 | 4 |
| Comp 3 | 0 | 0 | 1 |
| Comp 4 | 0 | 0 | 1 |
| Comp 5 | 0 | 0 | 1 |

EXAMPLES 56 AND 57

Sheath-core 3000 denier/100 filament yarns of nylon 6 were melt extruded using a die temperature of 280° C. and a draw ratio of 3.5. The filament sheath comprised about 25% of the fiber and contained the fluorochemical oxazolidinone (FC) of Example 1 in the amount (wt %) shown in Table 9. The filament core contained no fluorochemical additive. The yarn was tufted into carpet and tested for fluorine content (ppm). The carpet was mock dyed as in Examples 15-22 and again tested for fluorine content (ppm) and evaluated for walk-on-soiling (WOS). The results are set forth in Table 9.

TABLE 9

| Example No. | FC (wt. %) | F Content in sheath (ppm) | Fluorine content in carpet | | | WOS rating after indicated number of cycles | |
|---|---|---|---|---|---|---|---|
| | | | Before dyeing (ppm) | After dyeing (ppm) | Retention in fiber (%) | 1 | 2 |
| 56 | 0.25 | 1218 | 297 | 282 | 95 | 2 | 1 |
| 57 | 0.50 | 2435 | 589 | 588 | 100 | 4 | 6 |

EXAMPLES 58-65 AND COMPARATIVE EXAMPLES 6 and 7

In Examples 58-61, the fluorochemical oxazolidinone of Example 1 was dry mixed with polypropylene pellets (PP-3014, available from Exxon Co., melt flow index-12; average molecular weight, by GPC-161,000) in the amount shown in Table 10 and extruded as film using a 1-inch Wayne extruder, available from Wayne Machine and Die Co., and a 1.25 inch Killion die and tower, available from Killion Extruders, Inc. The films were extruded in the form of a tube of blown film of 20 cm circumference having a thickness of 2.5 mils (64 microns). The extruder temperatures were 200° C. (zone 1), 240° C. (zone 2), and 290° C. (zone 3), the melt temperature was 245° C. and the die temperature was 210° C. For Examples 62-65, portions of each film, Examples 58-61, respectively, were annealed at 120° C. for 10 minutes.

For Comparative Examples 6 and 7, polypropylene film containing no fluorochemical oxazolidinone was extruded as in Examples 58-61. For Comparative Example 7, the film was annealed as in Examples 62-65.

The fluorine content of each film was measured after extrusion. Each film was tested for surface energy, 180°

C. peel adhesion and tape bond. The results are shown in Table 10.

Comparative Example 9 had a surface energy of 37.6 dynes/cm.

TABLE 10

| Example | Amount FC (wt %) | F Content (ppm) | Surface energy (dynes/cm) Inside | Surface energy (dynes/cm) Outside | 180° Peel adhesion (N/dm) 0 | 180° Peel adhesion (N/dm) 1 Day | 180° Peel adhesion (N/dm) 7 Day | Tape bond (N/dm) |
|---|---|---|---|---|---|---|---|---|
| Comp 6 | 0 | 0 | 32.1 | 31.6 | 37 | 44 | 47* | 67 |
| 58 | 0.125 | 440 | 22.8 | 24.1 | 16 | 28 | 32 | 67 |
| 59 | 0.25 | 778 | 17.5 | 22.5 | 22 | 28 | 35 | 67 |
| 60 | 0.50 | 2360 | 16.3 | 23.4 | 22 | 32 | 35 | 63 |
| 61 | 1.00 | 3633 | 12.4 | 18.4 | 11 | 3–18* | 3–26* | 63 |
| Comp 7 | 0 | 0 | 31.9 | 31.3 | 28 | 45 | 48 | 67 |
| 62 | 0.125 | 440 | 11.7 | 12.4 | 18 | 25 | 24 | 63 |
| 63 | 0.25 | 778 | 10.7 | 12.9 | 14 | 23 | 24 | 63 |
| 64 | 0.50 | 2360 | 10.7 | 13.6 | 12 | 19 | 16 | 59 |
| 65 | 1.00 | 3633 | 10.5 | 12.2 | 2* | 2–7* | 0–3* | 56 |

*non-uniform peel

EXAMPLES 66–71 AND COMPARATIVE EXAMPLES 8

For Examples 66–71 polyvinyl chloride compositions were prepared containing 1740 g polyvinyl chloride (Geon TM 110×426, available from B. F. Goodrich Chem. Co.), 576 g plasticizer (Santicizer TM 441, available from Monsanto Chem. Co.), 360 g $TiO_2$ (Titanox TM 2160, available from National Lead Co.), 17.4 g organotin stabilizer, 34.8 g lubricant (Acryloid K 175, available from Rohm and Haas Co.), and the fluorochemical oxazolidinone of Example 1 in the amount set forth in Table 11. The compositions were mixed in a Gunther Papermeier KG high intensity mixer and extruded as pellets using a 3.2 mm die. For Comparative Example 8, a polyvinyl chloride composition was prepared as in Examples 66–71 except that no fluorochemical oxazolidinone was added. Films were extruded at the thickness indicated in Table 11 using a Brabender extruder (1.9 cm screw, 15 cm die slit) at temperatures of 170° C. (zone 1), 205° C. (zone 2), 205° C. (zone 3), 170° C. (adapter) and 180° C. (die). Samples were tested for fluorine content and surface energy. Portions of film were annealed at 125° C. for 5 minutes and 10 minutes and tested for surface energy. The results are set forth in Table 11.

TABLE 11

| Example | Amount FC (wt %) | F content (ppm) | Thickness (microns) | Surface energy (dynes/cm) Un-annealed | Surface energy (dynes/cm) Annealed 5 min | Surface energy (dynes/cm) Annealed 10 min |
|---|---|---|---|---|---|---|
| Comp 8 | 0 | 0 | 50 | 33.2 | 32.2 | 32.6 |
| 66 | 0.067 | 238 | 50 | 27.0 | 17.9 | 19.4 |
| 67 | 0.067 | 240 | 100 | 26.6 | 18.9 | 18.4 |
| 68 | 0.067 | 231 | 250 | 25.7 | — | — |
| 69 | 0.134 | 445 | 50 | 25.5 | 12.6 | 11.6 |
| 70 | 0.134 | 454 | 100 | 23.8 | 11.9 | 11.6 |
| 71 | 0.134 | 431 | 250 | 24.7 | — | — |

EXAMPLE 72 AND COMPARATIVE EXAMPLE 9

Polyester films were extruded at 125–250 microns thickness using polyethylene terephthalate pellets having a melt flow index of 6. For Example 72, 0.51 weight percent of the fluorochemical oxazolidinone of Example 1 was added to the melt. The film was tested for fluorine content and was found to contain 1705 ppm fluorine. For Comparative Example 9, no fluorochemical oxazolidinone was added to the melt. The surface energy of each film was tested. The film of Example 72 had a surface energy of 16.3 dynes/cm. The film of

EXAMPLE 73–77 AND COMPARATIVE EXAMPLE 10

Polypropylene films were extruded at thickness of 125 to 250 microns using the fluorochemical oxazolidinone (compound no. corresponding to example no.) in the amount set forth in Table 12. For Comparative Example 10, no fluorochemical oxazolidinone was added to the melt. The surface energy of each film was determined. The results are reported in Table 12.

TABLE 12

| Example | Compound | F content (ppm) | Surface energy (dynes/cm) |
|---|---|---|---|
| Comp 10 | — | 0 | 32.2 |
| 73 | 1 | 2500 | 12.4 |
| 74 | 6 | 2500 | 13.1 |
| 75 | 7 | 2500 | 11.7 |
| 76 | 7 | 1000 | 11.7 |
| 77 | 11 | 2500 | 12.4 |

EXAMPLES 78–80 AND COMPARATIVE EXAMPLE 11

Nylon 66 films were extruded at thickness of 125 to 250 microns using the fluorochemical oxazolidinone (compound no. corresponding to example no.) in the amount set forth in Table 13. For Comparative Example 11, no fluorochemical oxazolidinone was added to the melt. The surface energy of each film was determined, the results being set forth in Table 13.

TABLE 13

| Example | Compound | F content (ppm) | Surface energy (dynes/cm) |
|---|---|---|---|
| Comp 11 | — | 0 | 43.3 |
| 78 | 1 | 2500 | 11.3 |
| 79 | 3 | 2500 | 12.6 |
| 80 | 3 | 1000 | 14.5 |

EXAMPLES 81–88 AND COMPARATIVE EXAMPLES 8–15

The fluorochemical oxazolidinone of Example 1 was dry blended with polypropylene pellets (COSDEN resin: Dypro 8771, MFI=() at a fluorocarbon content of 0.5 weight percent. These mixtures were extruded into film with a 50 mm Rheotec single screw extruder. The extrusion conditions were: zone 1: 190° C., zone 2: 245° C., zone 3: 245° C., post mixing unit: 245° C., neck tube: 250° C., film die: 245° C. The screw speed was set at 60 rpm and the casting wheel at 12 rpm. The extruded films were 35.5 cm wide with a thickness of 0.127 mm. Two different casting wheel temperatures were used, 15° C. and 65° C. For comparison, a control film of pure polypropylene was produced at both conditions. Fluorine analysis and surface energy measurements were made. Both control films contained no fluorine and had a surface energy of 32 dynes/cm. The polypropylene film containing fluorochemical oxazolidinone cast at 15° C. contained 3600 ppm fluorine and had a surface energy of 13.1 dynes/cm while that cast at 65° C. contained 3000 ppm fluorine and had a surface energy of 12.9 dynes/cm. Each film was tested for release properties using the 180° peel adhesion test with the following pressure-sensitive adhesive tapes:

| Type A: | Scotch ® brand tape No. 8411, available from 3M Company (an acrylate adhesive on polyester film backing); |
|---|---|
| Type B: | Scotch ® brand tape No. KR 3252, available from 3M Company (a styrene/isoprene/styrene block copolymer adhesive on polypropylene backing); |
| Type C: | Scotch ® brand tape No. Y 4205, available from 3M Company (an acrylic-based foam tape) (previously adhered to and removed from a chrome plate); and |
| Type D: | Poly(dimethylsiloxane) adhesive (DC-355 available from Dow Corning Company) on polyester backing. |

The results are shown in Table 14.

TABLE 14

| Example | Casting roll (°C.) | Tape | 180° Peel adhesion (N/dm) 0 | 1 day | 7 days |
|---|---|---|---|---|---|
| Comp 8 | 15 | A | 18 | 17 | 17 |
| Comp 9 | 65 | A | 19 | 22 | 21 |
| 81 | 15 | A | 14 | 18 | 19 |
| 82 | 65 | A | 15 | 20 | 20 |
| Comp 10 | 15 | B | 37 | 34 | 34 |
| Comp 11 | 65 | B | 41 | 46 | 45 |
| 83 | 15 | B | 2 | 5 | 5 |
| 84 | 65 | B | 2 | 2 | 2 |
| Comp 12 | 15 | C | 31 | 36 | 36 |
| Comp 13 | 65 | C | 29 | 32 | 33 |
| 85 | 15 | C | 2 | 5 | 5 |
| 86 | 65 | C | 2 | 5 | 5 |
| Comp 14 | 15 | D | 49 | 48 | 52 |
| Comp 15 | 65 | D | 54 | 51 | 55 |
| 87 | 15 | D | 3 | 7 | 48 |
| 88 | 65 | D | 2 | 7 | 47 |

The data in Table 14 shows that the polypropylene film containing the fluorochemical oxazolidinone had excellent release properties with the adhesives of tapes B and C, excellent short-term release properties with the adhesive of tape D, but only marginal initial release properties with tape A.

EXAMPLES 89–100 AND COMPARATIVE EXAMPLES 16–27

A 0.2 weight percent solution of the fluorochemical oxazolidinone of Example 1 in N-methyl pyrrolidone (Examples 89–96) or methyl ethyl ketone (Examples 97–100) was applied to various substrates in a padding operation, the wet pickup being set forth in Table 15. Untreated substrates provided the comparative examples. The material of each example and comparative example were tested for fluorine content, oil repellency (OR), and water repellency (WR). The results are set forth in Table 15.

TABLE 15

| Example | Substrate | Wet pickup (ppm) | F content (ppm) | OR | WR |
|---|---|---|---|---|---|
| Comp 16 | Rayon knitted fabric | — | 0 | 0 | F |
| 89 | | 67 | 652 | 6 | 0 |
| Comp 17 | Nylon 66 carpet | — | 0 | 0 | F |
| 90 | | 50 | 487 | 4 | 3 |
| Comp 18 | Polypropylene upholstery fabric | — | 0 | 0 | 0 |
| 91 | | 50 | 487 | 1 | 0 |
| Comp 19 | Chrome tanned leather | — | 0 | 0 | F |
| 92 | | 40 | 390 | 4 | 2 |
| Comp 20 | Polypropylene carpet | — | 0 | 0 | F |
| 93 | | 35 | 341 | 4 | 2 |
| Comp 21 | Polyester drapery fabric | — | 0 | 0 | 0 |
| 94 | | 70 | 682 | 6 | 7 |
| Comp 22 | Polyester/cotton 80/20 fabric | — | 0 | 0 | F |
| 95 | | 30 | 292 | 3 | 2 |
| Comp 23 | Kevlar ™ fabric | — | 0 | 0 | 0 |
| 96 | | 47 | 458 | 2 | 3 |
| Comp 24 | Rayon upholstery fabric | — | 0 | 0 | F |
| 97 | | 87 | 847 | 4 | F |
| Comp 25 | Cotton fabric | — | 0 | 0 | F |
| 98 | | 59 | 762 | 2 | F |
| Comp 26 | Unsized cellulose paper | — | 0 | 0 | F |
| 99 | | 36 | 351 | 4 | 3 |
| Comp 27 | Cellulose/polyester (60/40) spun-laced non-woven | — | 0 | 0 | F |
| 100 | | 87 | 847 | 4 | 3 |

EXAMPLES 101–103 AND COMPARATIVE EXAMPLE 28

Melt-blown microfiber webs were prepared as described in Wente, Van A. "Superfine Thermoplastic Fibers", *Industrial and Engineering Chemistry*, vol. 48, no. 8, 1956, pp. 1342–1346 and Naval Research Laboratory Report 111437, Apr. 15, 1954 using polypropylene resin (Escorene pp 3085, melt fiber index: 35, available from Exxon Chemical Americas). In Examples 101–103, 0.2, 0.5 and 1.0 weight percent, respectively, of the fluorochemical oxazolidinone of Example 1 was added to the melt. In Comparative Example 28, no fluorochemical was added. The average fiber diameter was about 4 microns. Samples of web in each example were tested for fluorine content and basis weight. In Example 101 and Comparative Example 28, samples of the web were annealed at 130° C. for periods of 1 minute and five minutes. In Examples 102 and 103, samples of the web were annealed at 130° C. for 0.25, 0.5, 1 and 5 minutes. Unannealed and annealed samples were tested for water repellency (WR) and oil repellency (OR). The results were set forth in Table 16.

TABLE 16

| Example | FC content (wt. %) | F content (ppm) | Basis wt. (g/m$^2$) | Annealing time (min) | WR | OR |
|---|---|---|---|---|---|---|
| 101 | 0.2 | 446 | 54 | 0 | 3 | 0 |

TABLE 16-continued

| Example | FC content (wt. %) | F content (ppm) | Basis wt. (g/m²) | Annealing time (min) | WR | OR |
|---|---|---|---|---|---|---|
|  |  |  |  | 1 | 3 | 0 |
|  |  |  |  | 5 | 3 | 0 |
| 102 | 0.5 | 1209 | 55 | 0 | 3 | 0 |
|  |  |  |  | 0.25 | 4 | 1 |
|  |  |  |  | 0.5 | 4 | 1 |
|  |  |  |  | 1 | 5 | 3 |
|  |  |  |  | 5 | 6 | 5 |
| 103 | 1.0 | 3060 | 55 | 0 | 3 | 1 |
|  |  |  |  | 0.25 | 4 | 4 |
|  |  |  |  | 0.5 | 7 | 5 |
|  |  |  |  | 1 | 8 | 6 |
|  |  |  |  | 5 | 8 | 7 |
| Comp. 28 | 0 | 114 | 50 | 0 | 2 | 0 |
|  |  |  |  | 1 | 2 | 0 |
|  |  |  |  | 5 | 2 | 0 |

EXAMPLES 104–106 AND COMPARATIVE EXAMPLE 29

Melt-blown fiber webs were prepared as in Examples 104–106 and Comparative Example 29, except average fiber size was about 20 microns. Samples of each web were annealed at 130° C. for 5 minutes. The basis weight was determined for each web. Unannealed and annealed samples were tested for water repellency (WR) and oil repellency (OR). Results are set forth in Table 17.

TABLE 17

| Example | FC content (wt. %) | F content (ppm) | Basis wt. (g/m²) | Annealing time (min) | WR | OR |
|---|---|---|---|---|---|---|
| 104 | 0.2 | 566 | 50 | 0 | 3 | 0 |
|  |  | 392 |  | 5 | 9 | 6 |
| 105 | 0.5 | 1095 | 43 | 0 | 3 | 0 |
|  |  | 1050 |  | 5 | 9 | 7 |
| 106 | 1.0 | 2299 | 44 | 0 | 4 | 3 |
|  |  | 2164 |  | 5 | 9 | 7 |
| Comp. 29 | 0 | 100 | 45 | 0 | F | 0 |
|  |  | 94 |  | 5 | 2 | 0 |

EXAMPLES 107–109 AND COMPARATIVE EXAMPLE 30

Melt-blown fiber webs were prepared as in Examples 107–109 and Comparative Example 30, except that nylon resin (type 60H), available from Monsanto Co.) was substituted for the polypropylene and the fiber diameter was 40 microns. The basis weight of each web was determined. Samples of each web were annealed at 160° C. for 5 minutes. Unannealed and annealed samples were evaluated for fluorine content, water repellency and oil repellency. The results are set forth in Table 18.

TABLE 18

| Example | FC content (wt. %) | Basis wt. (g/m²) | Annealing time (min) | F content (ppm) | WR | OR |
|---|---|---|---|---|---|---|
| 107 | 0.2 | 79 | 0 | 583 | 1 | 0 |
|  |  |  | 5 | 640 | 7 | 6 |
| 108 | 0.5 | 82 | 0 | 1393 | 3 | 0 |
|  |  |  | 5 | 1566 | 8 | 7 |
| 109 | 1.0 | 88 | 0 | 3167 | 4 | 4 |
|  |  |  | 5 | 2425 | 9 | 7 |
| Comp. 30 | 0 | 88 | 0 | 51 | W | 0 |
|  |  |  | 5 | 69 | W | 0 |

The various modifications and alterations of this invention will be apparent to those skilled in the art without departing from the scope and spirit of this invention and this invention should not be restricted to that set forth herein for illustrative purposes.

What is claimed is:

1. Fluorochemical oxazolidinone compositions comprising normally solid, water-insoluble, fluoroaliphatic radical-containing 2-oxazolidinone compounds, said compounds comprising one or more 2-oxazolidinone moieties,

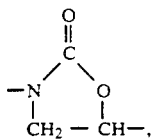

at least one of which has a monovalent fluoroaliphatic radical, $R_f$, which is fluorinated, stable, inert, non-polar, oleophobic, hydrophobic radical having 3 to 20 carbon atoms and 40 to 78 weight percent fluorine and the terminal portion of which has at least three fully fluorinated carbon atoms, bonded to the 5-position carbon atom of the 2-oxazolidinone moiety by a linking group, and a residue of an organic isocyanate exclusive of the isocyanate functional group bonded to the nitrogen atom of the 2-oxazolidinone moiety and said compound having 20 to 70 weight percent carbon-bonded fluorine.

2. Fluorochemical oxazolidinone compositions comprising normally solid, water-insoluble, fluoroaliphatic radical-containing 2-oxazolidinone compounds, said compounds are represented by the formula

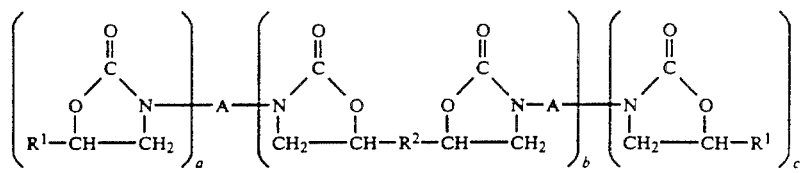

where each $R^1$ is independently hydrogen or an organic radical selected from alkyl, cycloalkyl, aryl and combinations thereof, said aryl radicals being aromatic hydrocarbon ring groups, and which organic radical can contain halogen atoms, one or more hetero atoms or hetero atom-containing moieties, and $-Q-R_f$ where Q is selected from $-CH_2-$, $-CH_2CH_2-$, $-CH_2CH(CH_2)-_2$, sulfonamidoalkylene, $-C_2H_4OCH_2-$, carbonamido, carbonamidoalkylene, carbonyloxy, urethane, and urylene, and $R_f$ is a fluorinated, saturated, monovalent, aliphatic, stable, nonpolar, inert, oleophobic, hydrophobic fluoroaliphatic radical having 3 to 20 carbon atoms and 40 to 78 weight percent fluorine and, each $R^2$ is independently an organic radical selected from alkylene groups, arylene groups, aralkylene groups and combinations thereof, said arylene groups being aromatic hydrocarbon ring groups, which organic radical, $R^2$, can contain said —Q—$R_f$ and one or more hetero atoms or hetero atom-containing moieties, with the proviso that there is at least one $R_f$ radical in one of $R^1$ and $R^2$, A is an organic radical selected form alkyl, aryl, aralkyl, alkylene, arylene, or aralkylene, and can contain one or more hetero atoms or hetero atom-containing moieties, said aryl, aralkyl, arylene, and aralkylene radicals having aromatic hydrocarbon ring groups, a is zero or 1, b is a number form 0 to about 6, c is 0, 1 or 2 and the sum of a+b+c is at least 1.

3. Fluorochemical oxazolidinone compositions according to claim 2, wherein $R^1$ is H—, $ClCH_2$—, $C_6H_5$—, $C_6H_5OCH_2$—, $C_8F_{17}SO_2N(CH_3)CH_2$—, $C_6F_{13}CH_2CH_2OCH_2$—, or $C_{10}F_{21}CH_2CH_2SCH_2CH_2OCH_2$—.

4. Fluorochemical oxazolidinone compositions according to claim 2 wherein $R^2$ is —$CH_2O(CH_2)_4OCH_2$—, —$CH_2OCOC_6H_4COOCH_2$—, —$CH_2OC_6H_4C(CH_3)_2C_6H_4OCH_2$—, $C_8F_{17}SO_2N(CH_2-)_2$, or $C_6F_{13}CON(CH_2-)_2$.

5. Fluorochemical oxazolidinone compositions according to claim 2 wherein A is $C_6H_5$—, $C_6H_4CH_2C_6H_4$—, —$CH_2C_6H_4CH_2$—, $C_6H_3(CH_3)$—, —$(CH_2)_6$—, —$C(CH_3)_2C_6H_4C(CH_3)_2$—, —$(CH_2)_6N_2$, —$C_6H_4CH_2C_6H_4CH_2C_6H_4$—, —$C_6H_{10}CH_2C_6H_{10}$—, or

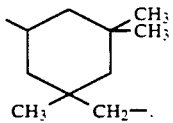

6. Fluorochemical oxazolidinone compositions according to claim 1 wherein said compound is represented by the formula

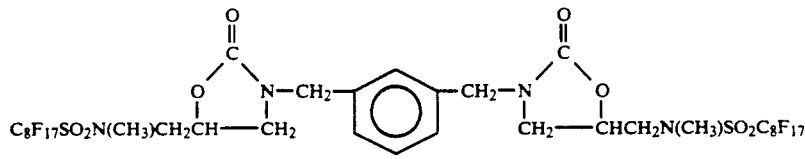

7. Fluorochemical oxazolidinone compositions comprising normally solid, water-insoluble, fluoroaliphatic radical-containing 2-oxazolidinone compounds, said compounds comprising one or more 2-oxazolidinone moieties,

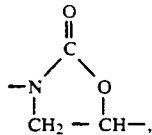

at least one of which has a monovalent fluoroaliphatic radical, $R_f$, which is fluorinated, stable, inert, non-polar, oleophobic, hydrophobic radical having 3 to 20 carbon atoms and 40 to 78 weight percent fluorine and the terminal portion of which has at least three fully fluorinated carbon atoms, bonded to the 5-position carbon atom of the 2-oxazolidinone moiety by a linking group which is selected from —$CH_2$—, —$CH_2CH_2$—, —$CH_2CH(CH_2-)_2$, —$C_2H_4OCH_2$—, sulfonamidoalkylene, carbonamido, carbonamidoalkylene, carbonyloxy, urethane, and urylene, and a residue of an organic isocyanate exclusive of the isocyanate functional group bonded to the nitrogen atom of the 2-oxazolidinone moiety and said compound having 20 to 70 weight percent carbon-bonded fluorine.

* * * * *

UNITED STATES PATENT AND TRADEMARK OFFICE
CERTIFICATE OF CORRECTION

PATENT NO. : 5,099,026                                  Page 1 of 2
DATED     : March 24, 1992
INVENTOR(S) : Richard D. Howells It is certified that error appears in the above-indentified patent and that said Letters Patent is hereby corrected as shown below:

On the Title Page, under item [19], change "Crater" to —Howells—; and item [76] should read as follows:
—Richard D. Howells, Richard M. Stern, both of P.O. Box 33427, St. Paul, Minn. 55133-3427—

| | |
|---|---|
| Col. 3, line 35 | "-$CH_2OC_6H_4(CH_3)_2C_6H_4OCH_2$-" should read -- -$CH_2OC_6H_4C(CH_3)_2C_6H_4ICH_2$- -- |
| Col. 4, line 1 | "[$CONH(CH_2)_6]_2$," should read -- [$CONH(CH_2)_6]_2$, -- |
| Col. 4, line 1 | "$C_8F_{17}SO_3C_6H$     4-," should read -- $C_8F_{17}SO_3C_6H_4$-, -- |
| Col. 4, line 29 | "su:h" should read -- such -- |
| Col. 4, line 49 | "Each-Q" should read -- Each Q -- |
| Col. 4, line 63 | "-$SO_2NR^4(CH_2)_3$" should read -- -$SO_2NR^4(CH_2)_3$ -- |
| Col. 5, line 37 | "$R_fSO_2N(R)H + CH_2CHCH_2Cl \longrightarrow \rangle$" should read -- $R_fSO_2N(R)H + CH_2CHCH_2Cl \longrightarrow R_fSO_2N(R)CH_2CH(CH_2Cl)OH$ -- |
| Col. 7, line 54 | "$C_8Fhd\ 17SO_2N(CH_3)H$" should read -- $C_8F_{17}SO_2N(CH_3)H$ -- |
| Col. 25, line 6 | "MFI=()" should read -- MFI=9) |
| Col. 28, line 64 | "-C2H$_4$OCH$_2$-" should read -- $C_2H_4OCH_2$ -- |

UNITED STATES PATENT AND TRADEMARK OFFICE
CERTIFICATE OF CORRECTION

PATENT NO. : 5,099,026

DATED : March 24, 1992

INVENTOR(S) : Davis H. Crater, et al

It is certified that error appears in the above-indentified patent and that said Letters Patent is hereby corrected as shown below:

Col. 29, line 44     "$C_6H_3(CH_3$," should read -- $C_6H_3(CH_3)$, --

Col. 29, line 45     "$-(CH_2)_6N_2$," should read

-- $-(CH_2)_6N[CONH(CH_2)_6-]_2$ --

Signed and Sealed this

Twenty-eight Day of February, 1995

Attest:

BRUCE LEHMAN

Attesting Officer     Commissioner of Patents and Trademarks